(12) United States Patent
Nagai et al.

(10) Patent No.: US 9,051,288 B2
(45) Date of Patent: Jun. 9, 2015

(54) METHOD FOR PRODUCING 4'-ETHYNYL D4T

(75) Inventors: Katsuyuki Nagai, Tokyo (JP); Shinya Kiguchi, Hyogo (JP); Hiroya Koyama, Hyogo (JP); William Ewan Hume, Hyogo (JP); Satoshi Tsujimoto, Hyogo (JP)

(73) Assignee: ONCOLYS BIOPHARMA, INC., Tokyo (JP)

( * ) Notice: Subject to any disclaimer, the term of this patent is extended or adjusted under 35 U.S.C. 154(b) by 668 days.

(21) Appl. No.: 12/810,608

(22) PCT Filed: Dec. 26, 2008

(86) PCT No.: PCT/JP2008/073783
§ 371 (c)(1),
(2), (4) Date: Jun. 25, 2010

(87) PCT Pub. No.: WO2009/084655
PCT Pub. Date: Jul. 9, 2009

(65) Prior Publication Data
US 2010/0280235 A1    Nov. 4, 2010

(30) Foreign Application Priority Data
Dec. 27, 2007  (JP) ................................. 2007-336334

(51) Int. Cl.
*C07D 405/04* (2006.01)
*C07D 307/32* (2006.01)
*C07D 307/33* (2006.01)

(52) U.S. Cl.
CPC ............ *C07D 307/32* (2013.01); *C07D 307/33* (2013.01); *C07D 405/04* (2013.01)

(58) Field of Classification Search
None
See application file for complete search history.

(56) References Cited

U.S. PATENT DOCUMENTS

| 5,041,566 A | 8/1991 | Shibagaki et al. |
| 2004/0167096 A1 | 8/2004 | Cheng et al. |

FOREIGN PATENT DOCUMENTS

| JP | 03-173891 | 7/1991 |
| JP | 05-213926 | 8/1993 |
| JP | 2006-528972 | 12/2006 |

OTHER PUBLICATIONS

Merriam-Webster Online Dictionary, "derivative"; also available at http://www.merriam-webster.com/dictionary/derivative; last viewed Jul. 15, 2009.*
Kazuhiro Haraguchi et al., "Synthesis of a highly active new anti-HIV agent 2'.3'-didehydro-3'-deoxy-4'-ethynylthymidi ne", Bioorganic & Medicinal Chemistry Letters, vol. 13 (2003), pp. 3775-3777.
Kazuhiro Haraguchi et al., "Nucleophilic substitution at the 4'-position of nucleosides: new access to a promising anti-HIV agent 2',3'-didehydro-3'-deoxy-4'-ethynylthymidi ne", J. Org. Chem., vol. 71, (2006), pp. 4433-4438.
Communication mailed by the European Patent Office on Oct. 28, 2011 in connection with counterpart application No. EP 08869172.0.
Chen et al., "Synthesis of 3'Fluoro-2', 3'-dideoxy . . . Nucleosides", J. of Organic Chem. 69(18):6034-6041 (2004).
Maddaford et al., "Stereoselective Synthesis of rac-4'Enthynyl-2'-deoxy- and . . . Analogues", Synthesis, 9:1378-1384 (2007).
Achmatowicz Jr., et al., "Synthesis of Methyl 2,3-Dideoxy-DL-Alk-2-Enopyranosides . . . Compounds", Tetrahedron 27:1973-1996.
Zhang et al., "Design, synthesis, and preliminary SAR study . . . benzylamine", Bioorganic & Medicinal Chemistry 14:3953-3966 (2006).
Marco van den Heuvel et al., "Optically Active . . . Esterification", Tetrahedron Letters 38(9):1655-1658 (1997).

* cited by examiner

*Primary Examiner* — Layla Bland
*Assistant Examiner* — Bahar Craigo
(74) *Attorney, Agent, or Firm* — Fish & Richardson P.C.

(57) ABSTRACT

Disclosed is a method for mass-producing 4'-ethynyl d4T (4'-ethynyl-2',3'-didehydro-3'-deoxythymidine) by a simpler process at low cost. Specifically disclosed is a method for producing 4'-ethynyl d4T, which is characterized by comprising a step for introducing a triple bond-containing group into a furfuryl alcohol derivative or a levoglucosenone, by reacting the furfuryl alcohol derivative or levoglucosenone with a certain compound, and a step for reacting a compound represented by the formula (III), which is obtained by the aforementioned step, with thymine.

7 Claims, 2 Drawing Sheets

METHOD FOR PRODUCING 4'-ETHYNYL D4T

FIELD OF THE INVENTION

The present invention relates to a method for producing 4'-ethynyl-2',3'-didehydro-3'-deoxythymidine (4'-ethynyl d4T) by using furfuryl alcohol or levoglucosenone as a starting material.

BACKGROUND OF THE INVENTION

Acquired immune deficiency syndrome (AIDS) is an immunodeficiency disease caused by human immunodeficiency virus (HIV) that infects and destroys the immune cells, which leads to acquired immunodeficiency. AIDS surpasses malaria and tuberculosis in deaths worldwide. According to the report from the UNAIDS (the joint United Programme on HIV/AIDS) in November, 2007, the number of infected people was estimated to be 33 million with deaths of more than 2 million only in 2007 ("2007 AIDS epidemic update" 19 Nov. 2007).

Drug therapy for HIV requires accurate and continuous drug use. This is because the effective drug level in the blood needs to be kept constant in order to suppress viral proliferation, and missing doses or time lag in taking doses could cause emergence or proliferation of drug-resistant viruses (see Non-Patent Reference 1). Thus, in order to ensure successful anti-HIV therapy, good patient adherence, that is, patient's active involvement in the decision-making process in the therapeutic approach and carrying out that therapeutic approach on patient's own initiative, is important (see Non-Patent Reference 2).

Although current mainstay for drug treatment is multi-drug therapy (HAART) that employs a combination of multiple drugs, there has been a problem of undesirable drug switch due to emergence of drug-resistant virus and side-effects.

Recently, 4'-ethynyl-2',3'-didehydro-3'-deoxythymidine (4'-ethynyl d4T) was developed as a new active substance for drugs that solve this problem (see Patent Reference 1), whose clinical trial is expected to commence in the United States in 2008. 4'-ethynyl d4T is also effective against multidrug-resistant viruses, and supposed to be highly safe with lower mitochondrial toxicity and thus expected to facilitate long-term drug use and continuous adherence.

Production of 4'-ethynyl d4T, however, has problems in that conventional synthetic methods (see Patent Reference 1 and Non-Patent Reference 3) require a number of synthetic steps, that their production cost is high, and that they are ill-suited to mass production.

[Patent Reference 1] Japanese Laid-Open Patent Application No. 2006-528972.

[Non-Patent Reference 1] Paterson D, et al., 6th Conference on Retroviruses and Opportunistic Infections, Chicago, III, 1999.

[Non-Patent Reference 2] Yoshino, The Journal of Therapy, Vol. 88, No. 12 (2006.12), p. 2903-2907.

[Non-Patent Reference 3] Maddaford, et al., Synthesis, 2007, No. 9, p. 1378-1384.

DISCLOSURE OF THE INVENTION

Problems to be Solved by the Invention

Accordingly, problems to be solved by the present invention is to provide the above-mentioned drug to a larger number of HIV-infected people for practical realization of cure for HIV infection by providing a method for producing 4'-ethynyl-2',3'-didehydro-3'-deoxythymidine (hereinafter referred to as "4'-ethynyl d4T") as an active substance of the drug in a simpler way, at lower cost and in large quantities.

Means for Solving the Problems

In order to solve the above-mentioned problems, the present inventors have gone through keen research and found that a method for producing 4'-ethynyl d4T via a particular intermediate compound (a compound represented by Formula (III) indicated below) by using furfuryl alcohol or levoglucosenone as a starting material could solve the above-described problem, thereby accomplishing the present invention.

Thus, the present invention relates to the followings.

(1) A raw material for producing 4'-ethynyl d4T, the material comprising furfuryl alcohol.

(2) A raw material for producing 4'-ethynyl d4T, the material comprising levoglucosenone.

(3) A compound represented by the following Formula (III):

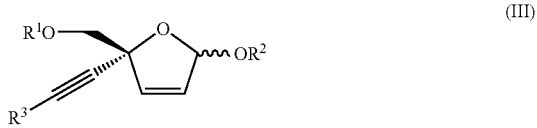

(wherein, $R^1$ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, $R^2$ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, and $R^3$ represents a hydrogen atom or a trisubstituted silyl group).

An example of the compound represented by Formula (III) above includes a compound wherein both $R^1$ and $R^2$ are hydrogen atoms, and $R^3$ is a trimethylsilyl group.

(4) A method for producing a compound represented by the following Formula (III):

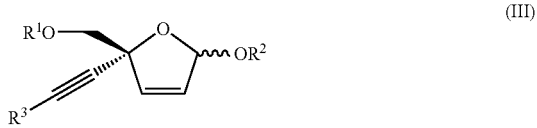

(wherein, $R^1$ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, $R^2$ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, and $R^3$ represents a hydrogen atom or a trisubstituted silyl group), the method comprising a step of introducing a triple bond-containing group into a furfuryl alcohol derivative or levoglucosenone by causing the furfuryl alcohol derivative or levoglucosenone to react with a compound represented by the following formula:

(wherein, R³ represents a hydrogen atom or a trisubstituted silyl group, and M represents a lithium atom, aluminum or monohalogenated magnesium).

(5) A method for producing 4'-ethynyl d4T, comprising a step of causing a compound represented by the following Formula (III) to react with thymine:

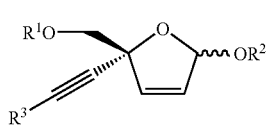

(wherein, R¹ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, R² represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, and R³ represents a hydrogen atom or a trisubstituted silyl group).

(6) A method for producing 4'-ethynyl d4T, comprising the steps of:
introducing a triple bond-containing group into a furfuryl alcohol derivative or levoglucosenone by causing the furfuryl alcohol derivative or levoglucosenone to react with a compound represented by the following formula:

(wherein, R³ represents a hydrogen atom or a trisubstituted silyl group, and M represents a lithium atom, aluminum or monohalogenated magnesium); and
causing the compound represented by the following Formula (III) resulting from the above step to react with thymine:

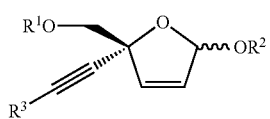

(wherein, R¹ represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, R² represents a hydrogen atom, an acyl group, an alkyl group, an alkenyl group, an aryl group, an aralkyl group, a cycloalkyl group, a heterocyclic group, a heterocyclic alkyl group or a trisubstituted silyl group, and R³ represents a hydrogen atom or a trisubstituted silyl group).

Effect of the Invention

The present invention can provide a method for producing 4'-ethynyl d4T in a simpler way, at lower cost and in larger quantities as compared to conventional methods.

Since 4'-ethynyl d4T can be an active substance of a drug that is effective in treating HIV infection, the production method of the invention is very useful for realizing practical application of therapies using this drug.

BEST MODES FOR CARRYING OUT THE INVENTION

Figure 1:
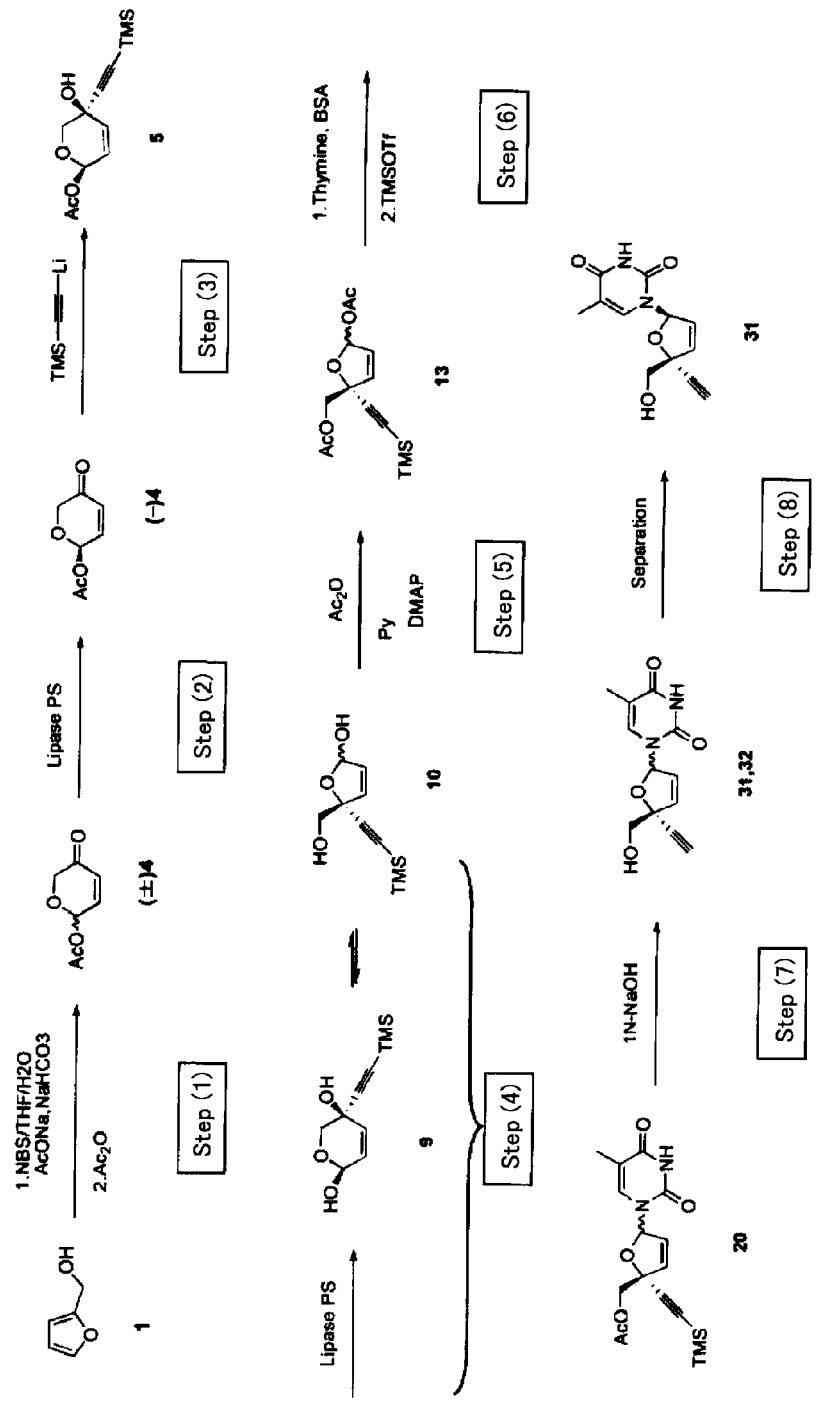
FIG. 1 shows a scheme for synthesizing 4'-ethynyl d4T by using furfuryl alcohol as a starting material.

Hereinafter, the present invention will be described in detail. The scope of the present invention should not be limited to these descriptions and the invention may be carried out in an appropriately modified way apart from the following examples without departing from the spirit of the invention. Moreover, all publications such as prior art documents, laid-open patent publications, patent publications and other patent documents cited herein are incorporated herein by reference.

1. Method for Producing 4'-ethynyl d4T by Using Furfuryl Alcohol as Starting Material
(1) Raw Material for Producing 4'-Ethynyl d4T
The present invention can provide a raw material for producing 4'-ethynyl d4T, the material comprising furfuryl alcohol represented by following Formula (I):

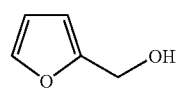

The raw material for production of the present invention may consist of furfuryl alcohol only, but without limitation, it may also comprise, for example, various reaction materials (reaction solutions, reaction substances) that can be used for obtaining an intermediate compound (a compound represented by Formula (III) indicated below) from furfuryl alcohol.

Here, examples of various reaction materials include solvents as typified by N-bromosuccinimide (NBS), tetrahydrofuran (THF), 1-butanol, n-hexane, acetonitrile and water, alkali metal salts as typified by sodium hydrogen carbonate and sodium acetate, acylating agents as typified by acetic anhydride and acetyl chloride, asymmetric hydrolases as typified by Lipase PS (lipase), and triple bond-containing compounds represented by the following formula:

(wherein, R³ represents a hydrogen atom or a trisubstituted silyl group, and M represents a lithium atom, aluminum or monohalogenated magnesium).

Examples of trisubstituted silyl groups include a trimethylsilyl group, a triethylsilyl group, a tert-butyldimethylsilyl group, a triisopropylsilyl group and a butyldiphenylsilyl group, among which a trimethylsilyl group is preferable.

In addition, examples of monohalogenated magnesium include magnesium chloride, magnesium bromide and magnesium iodide.

(2) Process of Producing Intermediate Compound

In the course of producing 4'-ethynyl d4T from furfuryl alcohol, the present invention can provide a method for producing a compound of the following Formula (III) as an intermediate compound of 4'-ethynyl d4T:

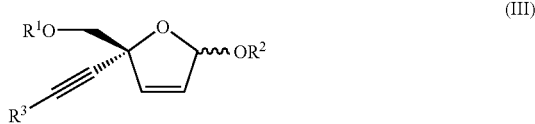

Specifically, a method for producing the compound of Formula (III) above can be provided, which comprises a step of introducing a triple bond-containing group into a furfuryl alcohol derivative by causing the furfuryl alcohol derivative to react with a compound represented by the following formula:

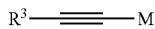

(wherein, $R^3$ represents a hydrogen atom or a trisubstituted silyl group and M represents a lithium atom, aluminum or monohalogenated magnesium (preferably, a lithium atom)).

As to Formula (III) above, examples of $R^1$ include a hydrogen atom, an acyl group, an alkyl group, an alkenyl group, an aryl group, an aralkyl group, a cycloalkyl group, a heterocyclic group, a heterocyclic alkyl group and a trisubstituted silyl group (preferably, a hydrogen atom or an acyl group).

Preferable examples of acyl groups as $R^1$ include an acetyl group, a benzoyl group, a propionyl group, a butyryl group, an isobutyryl group and a naphthoyl group, more preferably an acetyl group and a benzoyl group, and particularly preferably an acetyl group.

Preferable examples of alkyl groups as $R^1$ include a lower alkyl group with a carbon number of 1 to 6, more preferably a methyl group, an ethyl group, a propyl group, an isopropyl group, a butyl group, an isobutyl group and a tert-butyl group, and particularly preferably a methyl group.

Preferable examples of alkenyl groups as $R^1$ include a vinyl group, an allyl group, a 1-propenyl group, a 2-propenyl group and an isopropenyl group.

Preferable examples of aryl groups as $R^1$ include a phenyl group, an indenyl group, a 1-naphthyl group, a 2-naphthyl group, an azulenyl group, a heptalenyl group, an indacenyl group, an acenaphthyl group, a fluorenyl group, a phenalenyl group, a phenanthrenyl group and an anthracenyl group.

Preferable examples of aralkyl groups as $R^1$ include a benzyl group, a phenylethyl group, a phenylpropyl group, a naphthylmethyl group and a naphthylethyl group.

Preferable examples of cycloalkyl groups as $R^1$ include a cyclopropyl group, a cyclobutyl group, a cyclopentyl group, a cyclohexyl group, a cycloheptyl group and a cyclooctyl group.

Preferable examples of heterocyclic groups as $R^1$ include a pyrrolidinyl group, a pyrrolinyl group, an imidazolidinyl group, a pyrazolidinyl group, a pyrazolinyl group, a piperazinyl group and an indolinyl group.

Preferable examples of heterocyclic alkyl groups as $R^1$ include a 4-pyridylmethyl group, a 2-pyridylmethyl group, a 2-(4-pyridyl)ethyl group and a 2-imidazolylmethyl group.

Preferable examples of trisubstituted silyl groups as $R^1$ include a trimethylsilyl group, a triethylsilyl group, a tert-butyldimethylsilyl group, a triisopropylsilyl group and a butyldiphenylsilyl group, among which a trimethylsilyl group is more preferable.

As to Formula (III) above, examples of $R^2$ include a hydrogen atom, an acyl group, an alkyl group, an alkenyl group, an aryl group, an aralkyl group, a cycloalkyl group, a heterocyclic group, a heterocyclic alkyl group and a trisubstituted silyl group (preferably, a hydrogen atom or an acyl group).

Preferable examples of acyl groups as $R^2$ include an acetyl group, a benzoyl group, a propionyl group, a butyryl group, an isobutyryl group and a naphthoyl group, more preferably an acetyl group and a benzoyl group, and particularly preferably an acetyl group.

Preferable examples of alkyl groups as $R^2$ include a lower alkyl group with a carbon number of 1 to 6, a dimethoxytrityl group and a benzyl group, more preferably, a methyl group, an ethyl group, a propyl group, an isopropyl group, a butyl group, an isobutyl group and a tert-butyl group, and particularly preferably a methyl group.

Preferable examples of alkenyl groups as $R^2$ include a vinyl group, an allyl group, a 1-propenyl group, a 2-propenyl group and an isopropenyl group.

Preferable examples of aryl groups as $R^2$ include a phenyl group, an indenyl group, a 1-naphthyl group, a 2-naphthyl group, an azulenyl group, a heptalenyl group, an indacenyl group, an acenaphthyl group, a fluorenyl group, a phenalenyl group, a phenanthrenyl group and an anthracenyl group.

Preferable examples of aralkyl groups as $R^2$ include a benzyl group, a phenylethyl group, a phenylpropyl group, a naphthylmethyl group and a naphthylethyl group.

Preferable examples of cycloalkyl groups as $R^2$ include a cyclopropyl group, a cyclobutyl group, a cyclopentyl group, a cyclohexyl group, a cycloheptyl group and a cyclooctyl group.

Preferable examples of heterocyclic groups as $R^2$ include a pyrrolidinyl group, a pyrrolinyl group, an imidazolidinyl group, a pyrazolidinyl group, a pyrazolinyl group, a piperazinyl group and an indolinyl group.

Preferable examples of heterocyclic alkyl groups as $R^2$ include a 4-pyridylmethyl group, a 2-pyridylmethyl group, a 2-(4-pyridyl)ethyl group and a 2-imidazolylmethyl group.

Preferable examples of trisubstituted silyl groups as $R^2$ include a trimethylsilyl group, a triethylsilyl group, a tert-butyldimethylsilyl group, a triisopropylsilyl group and a butyldiphenylsilyl group, among which a trimethylsilyl group is more preferable.

Examples of $R^3$ in Formula (III) above include a hydrogen atom and a trisubstituted silyl group.

Preferable examples of trisubstituted silyl groups as $R^3$ include a trimethylsilyl group, a triethylsilyl group, a tert-butyldimethylsilyl group, a triisopropylsilyl group and a butyldiphenylsilyl group, among which a trimethylsilyl group is more preferable.

Examples of intermediate compounds represented by Formula (III) above include, particularly preferably those wherein both $R^1$ and $R^2$ are hydrogen atoms or acyl groups (particularly, acetyl groups), and $R^3$ is a trimethylsilyl group, and more preferably those wherein both $R^1$ and $R^2$ are hydrogen atoms, and $R^3$ is a trimethylsilyl group.

Hereinafter, a process of producing an intermediate compound of Formula (III) above from furfuryl alcohol will be illustrated in detail with reference to FIG. 1. The present invention, however, is not particularly limited to this example, and this process may be carried out through appropriate modification by techniques common to those skilled in the art such that desirable substituents ($R^1$, $R^2$ and $R^3$) are obtained in Formula (III) above.

(i) Oxidation and Acetylation (Step (1))

First, furfuryl alcohol as a starting material is dissolved in water and tetrahydrofuran (THF), and then cooled. In this case, the volume ratio of tetrahydrofuran to water is preferably 4 or higher, and particularly preferably 8 or higher. For this dissolution, ether, hexane, tert-butyl alcohol or the like may be used instead of THF. Cooling preferably takes place at 10° C. or lower, and more preferably at 0° C. or lower.

To the cooled solution above, a mixture of sodium hydrogen carbonate, sodium acetate and N-bromosuccinimide is added, followed by agitation. Here, for this addition, bromine, methanol or sulfuric acid may be used instead of the above mixture.

To the agitated solution above, acetic anhydride is added. The molar ratio of acetic anhydride to furfuryl alcohol used as a starting material is preferably 1-10, more preferably 1-5, and particularly preferably 4. In terms of shortening the time required for acetylation reaction, N,N-dimethyl-4-aminopyridine (DMAP) is preferably added in addition to acetic anhydride. Addition is preferably carried out at room temperature or lower, and more preferably 0° C. or lower. Following addition, the solution is heated to 20-55° C. (preferably room temperature) to pursue acetylation reaction. The reaction is carried out with agitation for 2-24 hours (preferably 2-16 hours).

At the end of the acetylation reaction, a saturated aqueous sodium hydrogen carbonate solution (or an aqueous sodium hydroxide solution or an aqueous potassium hydroxide solution) is added, and then the organic layer is extracted with an organic solvent such as ethyl acetate (or chloroform, dichloromethane, ether, hexane or the like) according to a known technique. Subsequently, the obtained organic layer is dried, concentrated (vacuum concentration) and purified (column purification) to obtain an acetylated compound (±) as a yellow-brown oily product. The pH upon addition of a saturated aqueous sodium hydrogen carbonate solution (or an aqueous sodium hydroxide solution or an aqueous potassium hydroxide solution) is preferably, 5.5-7.5, and particularly preferably 6.5.

(ii) Lipase Reaction (Optical Resolution) (Step (2))

Lipase is added to the compound obtained in Step (1) for reaction. Upon lipase addition, for example, 2-propanol (IPA), normal butanol, n-hexane, THF, water and the like are preferably added together. The reaction is carried out at 20-55° C. (preferably room temperature) with agitation for 2-164 hours (preferably 3-20 hours).

At the end of the reaction, the organic layer is extracted, washed, concentrated (vacuum concentration) and purified (column purification, silica gel filtration, recrystallization, etc.) according to a known technique to obtain one enantiomer of the acetylated compound (±) obtained in Step (1) in preference to the other.

Preferable examples of "furfuryl alcohol derivatives" according to a production method of the present invention include the acetylated compound (±) obtained in Step (1) and the acetylated compound (−) obtained in Step (2), among which the acetylated compound (−) is preferable.

(iii) Introduction of Triple Bond-Containing Group (Ethynylation) (Step (3))

First, trimethylsilyl acetylene and n-butyllithium are reacted in a solution to prepare a solution of the following compound.

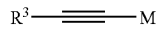

(in this particular case, $R^3$ represents a trimethylsilyl group, and M represents a lithium atom (Li)).

Specifically, trimethylsilyl acetylene is dissolved in THF (or an aprotic solvent such as ether, hexane or the like), and the internal temperature is reduced, to which a solution of n-butyllithium dispersed in n-hexane is added. Addition takes place while maintaining the internal temperature at 0° C. or lower (preferably −10° C. or lower, more preferably −20° C. or lower, and still more preferably −30° C. or lower). Then, the reaction solution is agitated at an internal temperature of about 0° C. for about an hour. Hence, the above-mentioned compound having a triple bond is obtained.

Next, to the solution of the compound having the triple bond, the acetylated compound (−) obtained in Step (2) is added for reaction. The molar ratio of the acetylated compound (−) to the above-mentioned compound having the triple bond is preferably 0.1-1, and more preferably 0.5-1. Preferably, addition takes place while maintaining the internal temperature at 0° C. or lower.

Following addition (following reaction), a mild acidic protic solvent (a saturated aqueous ammonium chloride solution, acetic acid, an acetic acid/THF solution or the like) is added and the solution is heated to room temperature. Thereafter, the organic layer is extracted, washed, dried, filtrated and concentrated (vacuum concentration) according to a known technique to obtain an acetylated compound (crude product) as a brown oily product. If necessary, the obtained crude product may be subjected to silica gel filtration, recrystallization and the like for purification.

(iv) Deacetylation Reaction (Step (4))

Next, the acetylated compound obtained in Step (3) is dissolved in acetonitrile (or normal butanol, n-hexane, 2-propanol or THF), to which an aqueous lipase solution is added and agitated for reaction. Agitation takes place while maintaining the temperature at 20-60° C. (preferably about 40° C.) for 8-48 hours (preferably 12-30 hours).

At the end of the reaction, saturated sodium hydrogen carbonate (or a saturated aqueous ammonium chloride solution) is added, and then the organic layer is extracted, washed, dried, filtrated, concentrated (vacuum concentration) and purified (column purification) according to a known technique to obtain a diol compound (mixture) as a yellow oily product having the compound of Formula (III) above (specifically, wherein $R^1$ and $R^2$ are hydrogen atoms, and $R^3$ is a trimethylsilyl group) as a part thereof. The compound of Formula (III), namely the intermediate compound of 4'-ethynyl d4T, included in this mixture may have two possible stereoisomers owing to asymmetric carbon atoms (anomeric carbons) at the C1-position where a hemiacetal hydroxyl group or an alkoxy group usually rest, which differ depending on the configuration of the hydroxyl group and the alkoxy group (alpha- and beta-configuration). The compound, however, is not limited to either of the stereoisomers and may be a mixture of both.

(v) Acetylation Reaction (Step (5))

Next, to the diol compound (mixture) obtained in Step (4), THF, acetic anhydride, pyridine and DMAP are added for acetylation reaction of the diol moiety. The reaction takes place at 10-40° C. (preferably about 30° C.) for 0.5-24 hours (preferably about an hour).

At the end of the reaction, the organic layer is extracted, washed, dried, filtrated and concentrated (vacuum concentration) according to a known technique to obtain an acetylated compound of Formula (III) above (specifically, wherein $R^1$ and $R^2$ are acetyl groups (Ac groups) and $R^3$ is TMS) as a brown oily product. The compound of Formula (III), namely the intermediate compound of 4'-ethynyl d4T, may have two possible stereoisomers owing to asymmetric carbon atoms (anomeric carbons) at the C1-position where a hemiacetal hydroxyl group or an alkoxy group usually rest, which differ depending on the configuration of the hydroxyl group and the alkoxy group (alpha- and beta-configuration). The compound, however, is not limited to either of the stereoisomers and may be a mixture of both.

(3) Process of Producing 4'-Ethynyl d4T

The present invention can provide a method for producing 4'-ethynyl d4T (Formula (IV) below), i.e., a compound of interest, from the compound of Formula (III) obtained by the steps in item 1.(2) above in the course of producing 4'-ethynyl d4T from furfuryl alcohol:

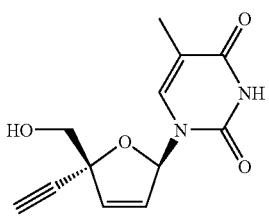

(IV)

Specifically, the invention can provide a method for producing 4'-ethynyl d4T comprising a step of causing the compound of Formula (III) above (particularly preferably, the compound of Formula (III) obtained in Step (5) above) to react with thymine.

Hereinafter, the process of producing 4'-ethynyl d4T from the compound of Formula (III) above will be illustrated in detail with reference to FIG. 1. The present invention, however, is not limited to this illustration, and this process may be carried out through appropriate modification by techniques common to those skilled in the art according to the type of the substituents ($R^1$, $R^2$ and $R^3$) of the compound of Formula (III).

(i) Nucleosidation (Thymine Introduction) (Step (6))

First, thymine and N,O-bis-trimethylsilyl acetamide or trimethylsilane chloride are added to 1,2-dichloroethane, heated under reflux, and cooled in advance. The solvent used is not limited to 1,2-dichloroethane, and chloroform, dichloromethane, tetrahydrofuran, or a mixed solvent thereof may also be used. Heating under reflux is carried out for 1-24 hours (preferably about 2 hours). Cooling after heating under reflux takes place at 10-30° C. (preferably about 20° C.).

Next, the acetylated compound obtained in Step (5) is dissolved in EDC (or halogenated hydrocarbon as typified by dichloromethane), which is added to the cooled solution above and agitated. Then, trimethylsilyl trifluoromethanesulfonate (TMSOTf) is further added and agitated for reaction. In this case, the molar ratio of the acetylated compound obtained in Step (5) to thymine used is preferably set to 0.5-1. The agitation following TMSOTf addition is carried out at 10-30° C. (preferably about 20° C.) for 1-24 hours (preferably about 2 hours).

At the end of the reaction, the organic layer is extracted, washed, dried, filtrated and concentrated (vacuum concentration) according to a known technique to obtain a crude product, which is subjected to slurry wash using a nonpolar hydrocarbon solvent such as n-hexane, thereby obtaining an acetylated compound as light brown crystal.

(ii) Deprotection (Step (7))

First, the acetylated compound obtained in Step (6) is added and dissolved in methanol, tetrahydrofuran, water, or a mixture solution thereof.

Next, an aqueous 1N-NaOH solution is added to the dissolved solution, and agitated for reaction. Agitation is carried out at 10-30° C. (preferably 20° C.) for 0.5-5 hours (preferably about an hour).

At the end of the reaction, the organic layer is extracted, dried, filtrated and concentrated (vacuum concentration) according to a known technique to obtain a compound (mixture) as pale yellow crystal. In this case, this mixture has a mixture of geometric isomers since the carbon atom that binds to a methylpyrimidine group among the carbon atoms of 4'-ethynyl d4T, i.e., the compound of interest, is an asymmetric carbon atom.

(iii) Separation/Purification (Step (8))

The compound (geometric mixture) obtained in Step (7) is subjected to slurry wash (ethyl acetate or the like) and recrystallization with methanol (or ethanol, ethyl acetate or ether) to obtain 4'-ethynyl d4T as the compound of interest. The number of recrystallization carried out is not limited but preferably twice or more.

Furthermore, at the end of the reaction at Step (7), the reaction product may be filtrated and thereafter purified by column purification at Step (8).

2. Method for Producing 4'-Ethynyl d4T by Using Levoglucosenone as Starting Material (1) Raw Material for Producing 4'-Ethynyl d4T The present invention can provide a raw material for producing 4'-ethynyl d4T, the material comprising levoglucosenone represented by following Formula (II):

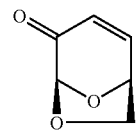

(II)

The raw material for production according to the present invention may consist of levoglucosenone only, but without limitation, it may also comprise, for example, various reaction materials (reaction solutions, reaction substances) that can be used for obtaining an intermediate compound (a compound represented by Formula (III) indicated below) from levoglucosenone.

Here, examples of various reaction materials include triple bond-containing compounds represented by the following formula:

(wherein, $R^3$ represents a hydrogen atom, a trimethylsilyl group, a triethylsilyl group, a tert-butyldimethylsilyl group, a triisopropylsilyl group or a butyldiphenylsilyl group, and M represents a lithium atom, aluminum or monohalogenated magnesium), acetic anhydride, hydrazine hydrate ($N_2H_4 \cdot H_2O$), sodium tetrahydroborate ($NaBH_4$), tert-butyl dimethylsilane chloride (TBSCl), sodium hydroxide, sodium periodate ($NaIO_4$) and water.

(2) Process of Producing Intermediate Compound

The present invention can provide a method for producing a compound of the following Formula (III), i.e., an intermediate compound of 4'-ethynyl d4T, in the course of producing 4'-ethynyl d4T from levoglucosenone:

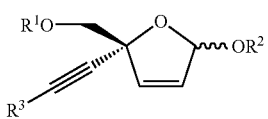

(III)

Specifically, the present invention provides a method for producing the compound of Formula (III) above, which comprises a step of introducing a triple bond-containing group into levoglucosenone by causing levoglucosenone to react with a compound represented by the following formula:

(wherein, $R^3$ and M are the same as indicated in item 1.(2) above).

In this case, $R^1$ in Formula (III) above is basically the same as described in item 1.(2) above, but preferably, it is a tert-butyldimethylsilyl group (TBS).

Moreover, $R^2$ and $R^3$ are the same as described in item 1.(2) above.

The intermediate compound represented by Formula (III) above is preferably a compound wherein $R^1$ is TBS, $R^2$ is a hydrogen atom or an acyl group (in particular, an acetyl group), and $R^3$ is a trimethylsilyl group, and more preferably a compound wherein $R^1$ is TBS, $R^2$ is a hydrogen atom, and $R^3$ is a trimethylsilyl group.

Figure 2:
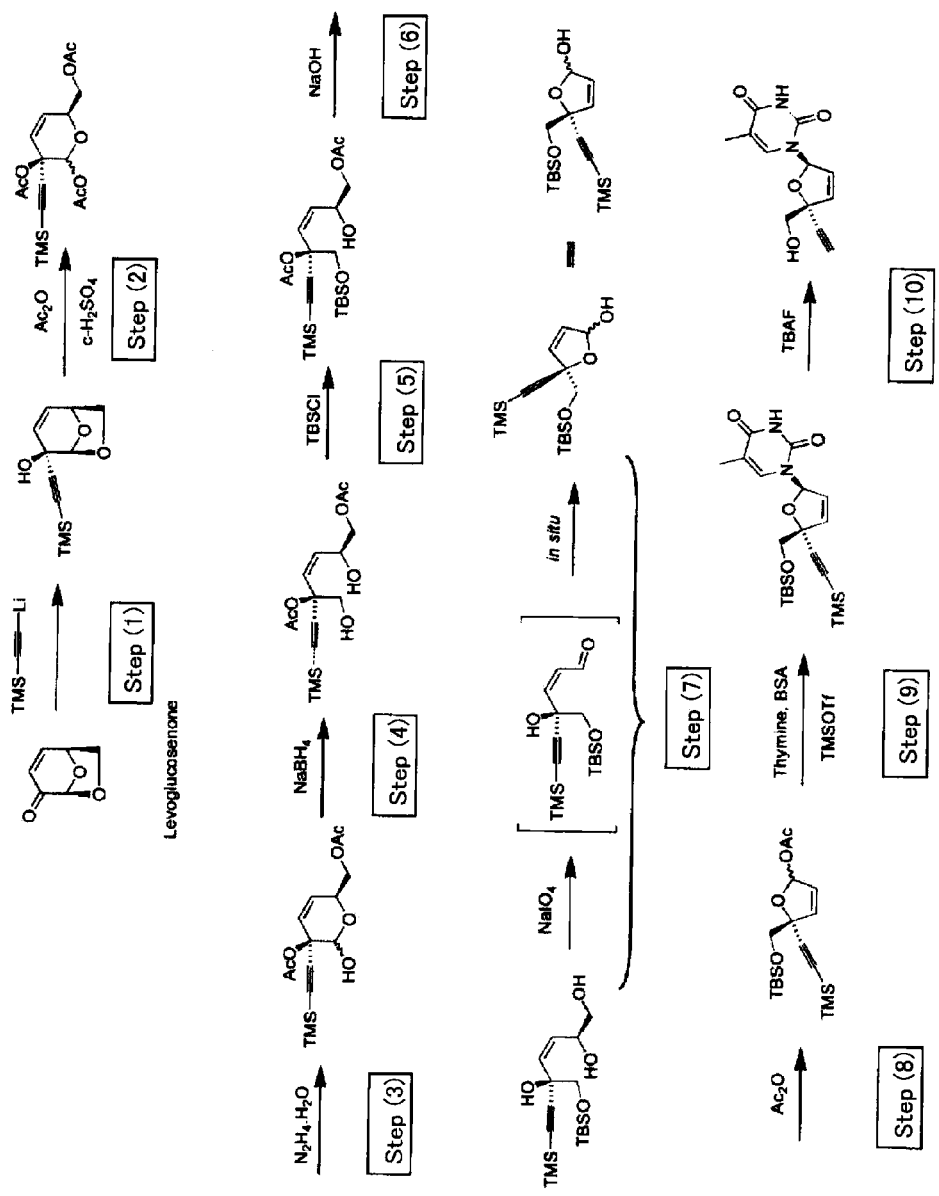
FIG. 2 shows a scheme for synthesizing 4'-ethynyl d4T by using levoglucosenone as a starting material.

Hereinafter, a process of producing an intermediate compound of Formula (III) above from levoglucosenone will be illustrated in detail with reference to FIG. 2. The present invention, however, is not particularly limited to this illustration, and this process may be carried out through appropriate modification by techniques common to those skilled in the art such that desirable substituents ($R^1$, $R^2$ and $R^3$) are obtained in Formula (III) above.

(i) Introduction of Triple Bond-Containing Group (Ethynylation) (Step (1))

First, trimethylsilyl acetylene and normal butyllithium are reacted in a solution in an inert gas stream (preferably, a nitrogen gas stream) to prepare a solution of the following compound:

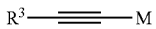

(in this case, $R^3$ represents a trimethylsilyl group (TMS), and M represents a lithium atom (Li)).

Specifically, trimethylsilyl acetylene is dissolved in THF (or ether, n-hexane or the like), and the internal temperature is reduced to −50 to −30° C. (preferably about −40° C.), to which the n-butyllithium hexane solution is added. Addition takes place while maintaining the internal temperature at −40 to −20° C. or lower (preferably −30° C. or lower). Then, the reaction solution is agitated at an internal temperature of about −40° C. to −20° C. (preferably about −30° C.) for 1-2 hours (preferably about an hour). Hence, the above-mentioned compound having a triple bond is obtained.

Next, to the solution of the triple bond-containing compound, levoglucosenone as a starting material is added for reaction. The molar ratio of levoglucosenone to the above-mentioned compound having the triple bond is preferably 0.1-1, and more preferably 0.5-1. Preferably, addition takes place while maintaining the internal temperature at 0° C. or lower, and more preferably at −30° C. or lower.

Following addition (at the end of the reaction), a saturated aqueous ammonium chloride solution is added and the resulting solution is heated to 20-35° C. (preferably room temperature). Thereafter, the organic layer is extracted, washed, dried, filtrated and concentrated (vacuum concentration) according to a known technique to obtain a compound (crude product) as a brown oily product.

(ii) Acetylation Reaction (Step (2))

The compound obtained in Step (1) is reacted with acetic anhydride in the presence of concentrated sulfuric acid.

At the end of the reaction, the organic layer is extracted, washed, dried, filtrated, concentrated (vacuum concentration) and if necessary purified (column purification) according to a known technique to obtain an acetylated compound.

(iii) Hydrolysis Reaction (Step (3))

The compound obtained in Step (2) is reacted in the presence of hydrazine.

At the end of the reaction, the organic layer is extracted, washed, dried, filtrated, concentrated (vacuum concentration) and if necessary purified (column purification) according to a known technique to obtain an acetylated compound.

(iv) Reduction Reaction (Step (4))

The compound obtained in Step (3) is reduced with sodium borohydride.

At the end of the reaction, the organic layer is extracted, washed, dried, filtrated, concentrated (vacuum concentration) and if necessary purified (column purification) according to a known technique to obtain an acetylated compound.

(v) Introduction of Protecting Group (Step (5))

The compound obtained in Step (4) is reacted with tert-butyl dimethylsilane chloride (TBSCl).

At the end of the reaction, the organic layer is extracted, washed, dried, filtrated, concentrated (vacuum concentration) and if necessary purified (column purification) according to a known technique to obtain a compound bearing TBS.

(vi) Deacetylation Reaction (Step (6))

The compound obtained in Step (5) is reacted in an aqueous sodium hydroxide solution.

At the end of the reaction, the organic layer is extracted, washed, dried, filtrated, concentrated (vacuum concentration) and if necessary purified (column purification) according to a known technique to obtain a triol compound.

(vii) Oxidation Reaction (Step (7))

The compound obtained in Step (6) is reacted with sodium periodate.

At the end of the reaction, the organic layer is extracted, washed, dried, filtrated, concentrated (vacuum concentration) and purified (column purification) according to a known technique to obtain the compound of Formula (III) above (specifically, wherein $R^1$ is TBS, $R^2$ is a hydrogen atom, and $R^3$ is TMS). The compound of Formula (III), namely the intermediate compound of 4'-ethynyl d4T, may have two possible stereoisomers owing to asymmetric carbon atoms (anomeric carbons) at the C1-position where a hemiacetal hydroxyl group or an alkoxy group usually rest, which differ depending on the configuration of the hydroxyl group and the alkoxy group (alpha- and beta-configuration). The compound, however, is not limited to either of the stereoisomers and may be a mixture of both.

(viii) Acetylation Reaction (Step (8))

Next, to the compound obtained in Step (7), tertiary aromatic amine such as acetic anhydride, pyridine or 4-dimethylaminopyridine is added in an inert gas stream (preferably, a nitrogen gas stream) for acetylation reaction of the hydroxy group. Reaction takes place at 25-35° C. (preferably about 30° C.) for 1-2 hours (preferably about an hour).

At the end of the reaction, the organic layer is extracted, washed, dried, filtrated and concentrated (vacuum concentration) according to a known technique to obtain an acetylated compound, i.e., a compound of Formula (III) above (specifically, wherein $R^1$ is TBS, $R^2$ is an acetyl group (Ac group), and $R^3$ is TMS). The compound of Formula (III), namely the intermediate compound of 4'-ethynyl d4T, may have two possible stereoisomers owing to asymmetric carbon atoms (anomeric carbons) at the C1-position where a hemiacetal hydroxyl group or an alkoxy group usually rest, which differ depending on the configuration of the hydroxyl group and the alkoxy group (alpha- and beta-configuration). The compound, however, is not limited to either of the stereoisomers and may be a mixture of both.

(3) Production Process of 4'-Ethynyl d4T

The present invention can provide a method for producing 4'-ethynyl d4T (following Formula (IV)), i.e., a compound of interest, from the compound of Formula (III) obtained by the step in item 2.(2) above in the course of producing 4'-ethynyl d4T from levoglucosenone.

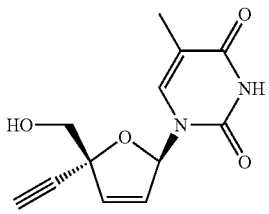

(IV)

Specifically, the invention can provide a method for producing 4'-ethynyl d4T, the method comprising a step of causing the compound of Formula (III) above (particularly preferably, the compound of Formula (III) obtained in Step (8) above) to react with thymine.

Hereinafter, the process of producing 4'-ethynyl d4T from the compound of Formula (III) above will be illustrated in detail with reference to FIG. 2. The present invention, however, is not limited to this illustration, and this process may be carried out through appropriate modification by techniques common to those skilled in the art according to the type of the substituents ($R^1$, $R^2$ and $R^3$) of the compound of Formula (III).

(i) Nucleosidation (Thymine Introduction) (Step (9))

First, thymine and N,O-bis-trimethylsilyl acetamide or trimethylsilane chloride is added to ethylene chloride or dichloromethane in an inert gas stream (preferably, a nitrogen gas stream), heated under reflux, and cooled in advance. Heating under reflux is carried out for 1-24 hours (preferably about 2 hours). Cooling after heating under reflux takes place at 10-30° C. (preferably about 20° C.).

Next, the acetylated compound obtained in Step (8) is dissolved in ethylene chloride or dichloromethane, and added to the cooled solution above and agitated. Then, trimethylsilyl trifluoromethanesulfonate (TMSOTf) is further added and agitated for reaction. In this case, the molar ratio of the acetylated compound obtained in Step (8) to thymine used is preferably set to 0.5-1. The agitation following TMSOTf addition is carried out at 10-30° C. (preferably about 20° C.) for 1-24 hours (preferably about 2 hours).

At the end of the reaction, the organic layer is extracted, washed, dried, filtrated and concentrated (vacuum concentration) according to a known technique to obtain a crude product, which is subjected to slurry wash (n-hexane, etc.), thereby obtaining a compound bearing TBS as light brown crystal.

(ii) Deprotection (Step (10))

First, the compound bearing TBS obtained in Step (9) is added and dissolved in a mixture solution of THF, ether and hexane in an inert gas stream (preferably, a nitrogen gas stream).

Next, tetrabutylammonium fluoride (TBAF) is added to and agitated in the dissolved solution above. Agitation is carried out at 20-30° C. (preferably room temperature) for 1-2 hours (preferably about an hour).

At the end of the reaction, the organic layer is extracted, dried, filtrated and concentrated (vacuum concentration) according to a known technique to obtain 4'-ethynyl d4T as the compound of interest.

3. Application of 4'-ethynyl d4T

4'-ethynyl d4T obtained according to the production method of the present invention is very useful as an active substance of a therapeutic agent for HIV infection.

When 4'-ethynyl d4T is used as an active substance of a therapeutic agent for AIDS, without limitation, it may be used in a form of salt, hydrate or the like as appropriate, or alternatively, it may be used after an appropriate chemical modification considering the preservation stability as a therapeutic agent.

The therapeutic agent may contain other substances in addition to 4'-ethynyl d4T. Examples of other substances include various pharmaceutically acceptable substances (various pharmaceutically acceptable carriers or the like) that are required depending on the usage (form of use) of the pharmaceutical composition. Other substances may appropriately be contained in a range that does not interfere with the therapeutic effect exhibited by 4'-ethynyl d4T.

As to the administration of the therapeutic agent, its mode is not limited, and a parenteral mode such as intravenous infusion is generally employed. Formulations that can be used for various modes such as parenteral modes may be prepared according to a routine method by appropriately selecting and using an excipient, a filler, a bulking agent, a binder, a wetting agent, a disintegrant, a lubricant, a surfactant, a dispersant, a buffer, a preservative, a solubilizing aid, an antiseptic, a flavoring agent, a soothing agent, a stabilizer, a tonicity agent and the like that are generally used for producing drugs. In addition, although the form of the therapeutic agent is not limited, intravenous injection (including infusion) is generally employed, for example, in a form of a unit dose ampule, a multi-dose container or the like.

In general, the dosage of the therapeutic agent may be determined appropriately and broadly according to the age, weight and condition of the administration subject (patient) as well as the route, time and period of administration in consideration of the proportion of the active substance in the agent.

Hereinafter, the present invention will be described more specifically by means of examples. The present invention, however, is not limited to these examples.

Example 1

Hereinafter, a first exemplary synthesis of 4'-ethynyl d4T using furfuryl alcohol as a starting material will be described (see Steps (1) to (8) in FIG. 1).

Abbreviations used in this example are as follows.
DMAP: 4-dimethylaminopyridine
BSA: N,O-bis-trimethylsilyl acetamide
EDC: 1,2-dichloroethane n-Hex: n-hexane
THF: tetrahydrofuran
AcOEt: ethyl acetate
TMSOTf: trimethylsilyl trifluoromethanesulfonate
IPA: 2-propanol 1. Step (1)

5,6-dihydro-5-oxo-2H-pyran-2-yl acetate (±) (Compound (±) 4)

500 g (5.10 mol) of furfuryl alcohol (Compound 1) was dissolved in 1.65 L of water and 6.6 L of THF in a nitrogen gas stream and cooled to 0° C. or lower. To this, a mixture of 855 g (10.2 mol) of sodium hydrogen carbonate, 418 g (5.10 mol) of sodium acetate and 953 g (5.35 mol) of N-bromosuccinimide was added by spending 40 minutes. Thereafter, the resultant was agitated for an hour, and 2,083 g (20.4 mol) of acetic anhydride was added at 0° C. or lower. Then, the resultant was heated to room temperature and agitated overnight. At the end of the reaction, 20.5 L of a saturated aqueous sodium hydrogen carbonate solution was added, followed by extraction with ethyl acetate. The organic layer was dried with anhydrous sodium sulfate and subjected to vacuum concentration to obtain 776 g of a crude product (crude yield: 42.6%). The obtained crude product was subjected to column purification (n-Hex:AcOEt=3:1) to obtain 339 g of Compound (±) 4 as a yellow-brown oily product.

Compound (±) 4:
$^1$H-NMR
δH (500 MHz; CDCl3) 6.93 (dd, 1H, J=10.5 and 3.5), 6.50 (d, 1H, J=3.5), 6.28 (d, 1H, J=10.5), 4.52 (d, 1H, J=17.5), 4.23 (d, 1H, J=17.5), 2.15 (s, 3H).

2. Step (2)

(R)-5,6-dihydro-5-oxo-2H-pyran-2-yl acetate (−) (Compound (−) 4)

To 336 g (2.15 mol) of the acetylated form (±) (Compound (±) 4), 67.2 g of Lipase PS Amano SD, 4.7 L of normal butanol, 15.5 L of n-hexane and 670 mL of water were added in a nitrogen gas stream, and agitated at room temperature overnight. At the end of the reaction, 6.7 L of water was added, followed by extraction with ethyl acetate. The extracted organic layers were mixed together, washed with saturated saline and subjected to vacuum concentration to obtain 246 g of a crude product (crude yield: 20.5%). The obtained crude product was subjected to column purification (n-Hex:AcOEt=3:1), and then the obtained crystal was washed with n-Hex/AcOEt=19/1 to obtain 69 g of Compound (−) 4 as white crystal. The result from optical rotation measurement was [α]20D=−184.53° (c=1.015, CHCl3), confirming that only Compound (−) 4 of interest was obtained.

Compound (−) 4:
$^1$H-NMR
δH (500 MHz; CDCl$_3$) 6.93 (dd, 1H, J=10.5 and 3.5), 6.50 (d, 1H, J=3.5), 6.28 (d, 1H, J=10.5), 4.52 (d, 1H, J=17.5), 4.23 (d, 1H, J=17.5), 2.15 (s, 3H).

3. Step (3)

(2R,5R)-5,6-dihydro-5-hydroxy-5-(2-(trimethylsilyl)ethynyl)-2H-pyran-2-yl acetate (Compound 5)

50.1 g (510 mmol) of trimethylsilyl acetylene was dissolved in 460 mL of THF in a nitrogen gas stream, and the internal temperature was reduced to −40° C. To this, 317 mL of 1.6 M n-butyllithiumhexane solution was allowed to fall in drops at −30° C. or lower by spending 40 minutes. The reaction solution was agitated at −30° C. for an hour, 66.0 g of the alcohol (−) (Compound (−) 4)/460 mL of THF was allowed to fall in drops at −30° C. or lower by spending 10 minutes. At the end of the reaction, a saturated aqueous ammonium chloride solution was added, and heated to room temperature. Water was added to the reaction solution, followed by extraction with ethyl acetate. The organic layer was washed with a saturated aqueous sodium chloride solution, dried with anhydrous sodium sulfate, filtrated and subjected to vacuum concentration to obtain 102.4 g of Compound 5 as a brown oily product (crude yield: 95.9%). Compound 5 as a crude product was directly used in the subsequent Step (4).

Compound 5:
$^1$H-NMR
δH (500 MHz; CDCl$_3$) 6.26 (dd, 1H, J=2.5 and 1.0), 6.11 (td, 1H, J=10.0 and 2.5), 5.77 (dd, 1H, J=10.0 and 2.5), 3.93 (dd, 1H, J=11.0 and 1.0), 3.86 (dd, 1H, J=11.0 and 0.5), 2.26 (s, 1H), 2.10 (s, 3H), 0.17 (s, 9H).

4. Step (4)

(2S,5R)-5,6-dihydro-5-(2-(trimethylsilyl)ethynyl)-2H-pyran-2,5-diol (Compound 9)

(R)-2,5-dihydro-5-(hydroxymethyl)-5-(2-(trimethylsilyl)ethynyl)furan-2-ol (Compound 10)

400 mL of an aqueous solution containing 9.8 g of Lipase PS Amano SD was added to a solution of 98.4 g (387 mmol) of the acetylated form (Compound 5) dissolved in 300 mL of acetonitrile, and agitated at 40° C. overnight. At the end of the reaction, a saturated aqueous sodium hydrogen carbonate solution was added, followed by extraction with ethyl acetate. The organic layer was washed with saturated saline, dried with anhydrous sodium sulfate, filtrated, and subjected to vacuum concentration to obtain 84.2 g of a crude product (crude yield: 75.8%). The obtained crude product was subjected to column purification (n-Hex:AcOEt=3:1) to obtain 62.3 g of a mixture of Compounds 9 and 10 as a yellow oily product.

Mixture of Compounds 9 and 10:
$^1$H-NMR
δH (500 MHz; CDCl$_3$) 6.12 (t, 0.63H, J=1.0), 6.10 (dd, 0.21H, J=6.0 and 1.5), 6.03 (m, 0.42H), 6.00 (dd, 0.63H, J=6.0 and 1.0), 5.97 (dd, 0.63H, J=6.0 and 1.0), 5.89 (dd, 0.09H, J=10.0 and 3.0), 5.83 (dd, 0.07H, J=10.0 and 2.0), 5.39 (d, 0.09H, J=2.0), 5.35 (t, 0.07H, J=1.0), 4.25 (d, 0.09H, J=12.0), 4.06 (t, 0.06H, J=7.0), 3.98 (d, 0.07H, J=12.0), 3.85 (d, 0.07H, J=12.0), 3.82 (dd, 0.09H, J=12.0 and 1.5), 3.77 (d, 0.63H, J=12.0), 3.76 (d, 0.21H, J=12.0), 3.68 (d, 0.63H, J=12.0), 3.67 (d, 0.21H, J=12.0), 0.174 (s, 1.44H), 0.170 (s, 7.56H).

5. Step (5)

(2R)-2,5-dihydro-5-acetoxy-2-(2-(trimethylsilyl)ethynyl)furan-2-yl)methyl acetate (Compound 13

260 mL of pyridine, 68.9 g (675 mmol) of acetic anhydride and 3.42 g (28 mmol) of DMAP were added to 59.3 g (279 mmol) of the diol compound (the mixture of Compounds 9 and 10) in a nitrogen gas stream, to allow reaction at 30° C. for an hour. At the end of the reaction, water and ethyl acetate were added for separation. The organic layer was washed with 1N-HCl and further washed with water. The organic layer was dried with anhydrous sodium sulfate, filtrated, and subjected to vacuum concentration to obtain 76.6 g of Compound 13 as a brown oily product (crude yield: 92.6%).

Compound 13:
$^1$H-NMR

δH (500 MHz; CDCl$_3$) 6.91 (t, 0.79H, J=1.0), 6.85 (t, 0.21H, J=1.0), 6.15 (dd, 0.21H, J=5.5 and 1.0), 6.00 (dd, 0.21H, J=5.5 and 1.0), 6.14 (dd, 0.79H, J=5.5 and 1.0), 5.96 (dd, 0.791-1, J=5.5 and 1.0), 4.39 (d, 0.21H, J=11.5), 4.35 (d, 0.79H, J=11.5), 4.25 (d, 0.79H, J=11.5), 4.19 (d, 0.21H, J=11.5), 2.10 (s, 0.63H), 2.09 (s, 2.37H), 2.05 (s, 0.63H), 2.07 (s, 2.37H), 0.17 (s, 1.89H), 0.16 (s, 7.11H).

6. Step (6)

(R)-2,5-dihydro-5-(3,4-dihydro-5-methyl-2,4-dioxopyrimidin-1(2H)-yl)-2-(2-(trimethylsilyl)ethynyl)furan-2-yl)methyl acetate (Compound 20

25.4 g (202 mmol) of thymine and 124 g (607 mmol) of BSA were added to 1.5 L of EDC in a nitrogen gas stream, heated under reflux for two hours, and then cooled to 20° C. A solution of 30.1 g (101 mmol) of the acetylated form (Compound 13) dissolved in 1.5 L of EDC was added and agitated for 10 minutes. Subsequently, 29.4 g (132 mmol) of TMSOTf was added and agitated at 20° C. for two hours. At the end of the reaction, water and ethyl acetate were added for separation. The organic layer was washed with water and a saturated aqueous sodium hydrogen carbonate solution. The organic layer was dried with anhydrous sodium sulfate, filtrated, and subjected to vacuum concentration to obtain 34.0 g of a crude product (crude yield: 24.0%). The obtained crude product was subjected to slurry wash with n-hexane to obtain 27.8 g of Compound 20 as light brown crystal.

Compound 20:
$^1$H-NMR

δH (500 MHz; CDCl$_3$) 8.09 (brs, 0.43H), 8.05 (brs, 0.57H), 7.20 (d, 0.57H, J=1.0), 7.24 (d, 0.43H, J=1.0), 7.10 (dd, 0.43H, J=2.0 and 1.5), 7.05 (t, 0.57H, J=1.5), 6.21 (dd, 0.43H, J=4.0 and 2.0), 6.19 (dd, 0.57H, J=4.0 and 2.0), 5.94 (t, 0.57H, J=1.5), 5.93 (t, 0.43H, J=1.5), 4.57 (d, 0.43H, J=12.0), 4.42 (d, 0.57H, J=12.0), 4.23 (d, 0.57H, J=12.0), 4.22 (d, 0.43H, J=12.0), 2.10 (s, 1.29H), 2.08 (s, 1.71H), 1.920 (s, 1.71H), 1.918 (s, 1.29H), 0.20 (s, 5.13H), 0.18 (s, 3.87H).

7. Step (7)

1-((2R,5R)-5-ethynyl-2,5-dihydro-5-(hydroxymethyl)furan-2-yl)-5-methylpyrimidine-2,4(1H,3H)-dione (Compound 31; β-form)

1-((2S,5R)-5-ethynyl-2,5-dihydro-5-(hydroxymethyl)furan-2-yl)-5-methylpyrimidine-2,4(1H,3H)-dione (Compound 32; α-form)

4.36 g (12.0 mmol) of the acetylated form (Compound 20) was added and dissolved in a mixture of 35 mL of methanol, 18 mL of THF and 5 mL of water in a nitrogen gas stream. 11.5 mL of an aqueous 1N-NaOH solution was added and agitated at room temperature for an hour. After confirming the end of the reaction, a saturated aqueous ammonium chloride solution was added, followed by extraction with ethyl acetate. The organic layer was dried with anhydrous sodium sulfate, filtrated and subjected to vacuum concentration to obtain 2.98 g of a mixture of Compounds 31 and 32 as pale yellow crystal (crude yield: 29.5%).

8. Step (8)

1-((2R,5R)-5-ethynyl-2,5-dihydro-5-(hydroxymethyl)furan-2-yl)-5-methylpyrimidine-2,4(1H,3H)-dione (Compound 31; β-form)

2.98 g of the mixture of Compounds 31 and 32 was subjected to slurry wash with ethyl acetate to obtain a product for 0.86 g. The obtained product of 0.86 g was recrystallized with 40 mL of methanol to obtain 253 mg of white crystal. The obtained crystal was again recrystallized with 22 mL of methanol to obtain 141 mg of intended Compound 31, namely 4'-ethynyl d4T, as white crystal (yield 16.0%).

Compound 31:
$^1$H-NMR

δH (500 MHz; DMSO-d6) 11.36 (brs, 1H), 7.58 (d, 1H, J=1.0), 6.88 (t, 1H, J=2.0), 6.35 (dd, 1H, J=5.5 and 2.0), 6.05 (dd, 1H, J=5.5 and 1.0), 5.47 (t, 1H, J=6.0), 3.69 (dd, 1H, J=12.5 and 6.0), 3.67 (s, 1H), 3.59 (dd, 1H, J=12.5 and 6.0), 1.71 (s, 3H).

$^1$H-NMR

δH (500 MHz; CD3OD) 7.71 (d, 1H, J=1.5), 7.03 (t, 1H, J=1.5), 6.32 (dd, 1H, J=6.0 and 2.0), 6.00 (dd, 1H, J=6.0 and 1.5), 3.82 (d, 1H, J=12.5), 3.75 (d, 1H, J=12.5), 3.08 (s, 1H), 1.82 (d, 3H, J=1.5).

$^{13}$C-NMR

δC (125 MHz; DMSO-d6) 164.54, 151.51, 137.49, 136.23, 127.82, 109.72, 89.61, 87.28, 82.14, 78.12, 66.44, 12.92.

Compound 32:
$^1$H-NMR

δH (500 MHz; DMSO-d6) 7.01 (s, 1H), 6.93 (s, 1H), 6.30 (d, 1H, J=5.5), 6.02 (d, 1H, J=5.5), 5.28 (brs, 1H), 3.80 (s, 1H), 3.54 (s, 2H), 1.71 (s, 3H).

$^1$H-NMR. δH (500 MHz; CD3OD) 7.34 (d, 1H, J=1.5), 7.00 (t, 1H, J=1.5), 6.34 (dd, 1H, J=6.0 and 2.0), 6.04 (dd, 1H, J=6.0 and 1.5), 3.73 (s, 1H), 3.72 (s, 1H), 3.31 (s, 1H), 1.86 (d, 3H, J=1.5).

$^{13}$C-NMR

δC (125 MHz; DMSO-d6) 135.19, 128.37, 110.41, 90.41, 87.04, 82.63, 79.40, 67.20, 13.82.

Example 2

Hereinafter, a second exemplary synthesis of 4'-ethynyl d4T using furfuryl alcohol as a starting material will be described (see Steps (1) to (8) in FIG. 1).

1. Step (1)

5,6-dihydro-5-oxo-2H-pyran-2-yl acetate (±) (compound (±) 4)

2055 g of sodium hydrogen carbonate and 1004 g of sodium acetate were dissolved in a mixed solvent of 1.8 L of water and 15 L of THF. The resultant was cooled to −15° C., and 1.2 L of THF solution containing 2257 g of N-bromosuccinimide was added while maintaining the temperature at 0° C. or lower. Furthermore, 1200 g of furfuryl alcohol (Compound 1) was added while maintaining the temperature at 0° C. or lower, and agitated at the same temperature for 10 minutes. After confirming the end of the reaction by thin-layer chromatography, 299 g of DMAP and 2498 g of acetic anhydride were added while maintaining the temperature at 0° C. or lower. The reaction solution was heated to 30° C. and agitated at that temperature for 3.5 hours. After confirming the end of the reaction by thin-layer chromatography, the solution was cooled to 5° C., and added with 9.5 L of 2 N aqueous sodium hydroxide solution to prepare a solution of pH 6.5. This reaction solution was extracted with ethyl acetate and washed with a saturated sodium bicarbonate solution to obtain the organic layer. The solvent was distilled away under reduced pressure to obtain 1263 g of a crude product (±) 4 as a clear brown oily product (crude yield: 71.1%).

Compound (±) 4:
$^1$H-NMR
δH (500 MHz; CDCl3) 6.93 (dd, 1H, J=10.5 and 3.5), 6.50 (d, 1H, J=3.5), 6.28 (d, 1H, J=10.5), 4.52 (d, 1H, J=17.5), 4.23 (d, 1H, J=17.5), 2.15 (s, 3H).

2. Step (2)

(R)-5,6-dihydro-5-oxo-2H-pyran-2-yl acetate (−) (compound (−) 4)

1351 g of Compound (±) 4 was dissolved in 27 L of IPA in a nitrogen gas stream. To this, 2.7 L of an aqueous solution of 135 g of Lipase PS Amano SD was added and agitated at 30° C. for 2.5 hours. After confirming the end of the reaction by liquid chromatography, solid matter was filtrated away. Following thorough wash with 1 L of water and 2 L of IPA, the obtained solution was concentrated under reduced pressure. 3 L of water was added to the concentrated solution, which was subjected to extraction with toluene. The organic layer was washed with a saturated sodium bicarbonate solution, and concentrated under reduced pressure to obtain 540 g of a crude product as an oily product. 445 g of this oily product was filtrated with silica gel, and the obtained crude product was recrystallized from IPA to obtain 243 g of Compound (−) 4 as white crystal (yield 21.8%). The result from optical rotation measurement was [α]20D=−184.53° (c=1.015, CHCl3), confirming that only Compound (−) 4 of interest was obtained.

Compound (−) 4:
$^1$H-NMR
δH (500 MHz; CDCl$_3$) 6.93 (dd, 1H, J=10.5 and 3.5), 6.50 (d, 1H, J=3.5), 6.28 (d, 1H, J=10.5), 4.52 (d, 1H, J=17.5), 4.23 (d, 1H, J=17.5), 2.15 (s, 3H).

3. Step (3)

(2R,5R)-5,6-dihydro-5-hydroxy-5-(2-(trimethylsilyl) ethynyl)-2H-pyran-2-yl acetate (Compound 5)

159 g of trimethylsilyl acetylene was dissolved in 1475 mL of dry THF and cooled to −30° C. or lower. To this, 1020 mL of a 1.6 M normal butyllithiumhexane solution was added while cooling to −30° C. or lower, and agitated for an hour. To this solution, 1475 mL of dry THF solution containing 210 g of Compound (−) 4 was added at −30° C. or lower and agitated for 30 minutes. After confirming the end of the reaction by thin-layer chromatography, 584 mL of a THF solution containing 116 g of acetic acid was added while maintaining the temperature at 30° C. or lower. 1 L of water was further added to separate the organic layer. The organic layer was washed sequentially with a saturated sodium bicarbonate solution and water, and concentrated under reduced pressure to obtain 324 g of a crude acetylated form 5 as an oily product. 322 g of this oily product was further filtrated with silica gel, and the obtained crude product was recrystallized from heptane to obtain 195 g of Compound 5 (Compound 5:5'=95.5: 4.5) as pale yellow crystal (yield 56.9%).

Compound 5:
$^1$H-NMR
δH (500 MHz; CDCl$_3$) 6.26 (dd, 1H, J=2.5 and 1.0), 6.11 (td, 1H, J=10.0 and 2.5), 5.77 (dd, 1H, J=10.0 and 2.5), 3.93 (dd, 1H, J=11.0 and 1.0), 3.86 (dd, 1H, J=11.0 and 0.5), 2.26 (s, 1H), 2.10 (s, 3H), 0.17 (s, 9H).

4. Step (4)

(2S,5R)-5,6-dihydro-5-(2-(trimethylsilyl)ethynyl)- 2H-pyran-2,5-diol (Compound 9)

(R)-2,5-dihydro-5-(hydroxymethyl)-5-(2-(trimethyl- silyl)ethynyl)furan-2-ol (Compound 10)

570 mL of an acetonitrile solution containing 190 g of Compound 5 was heated to 40° C., to which 760 mL of an aqueous solution containing 19 g Lipase PS Amano SD was added and the resultant was agitated for 15 hours while maintaining the temperature at 40° C. After confirming the end of the reaction by thin-layer chromatography, the resultant was left to cool at room temperature, added with water and subjected to extraction with ethyl acetate. The organic layer was concentrated to obtain 148 g of a mixture of Compounds 9 and 10 as a clear brown oily product (crude yield: 93.8%).

Mixture of Compounds 9 and 10:
$^1$H-NMR
δH (500 MHz; CDCl$_3$) 6.12 (t, 0.63H, J=1.0), 6.10 (dd, 0.21H, J=6.0 and 1.5), 6.03 (m, 0.42H), 6.00 (dd, 0.63H, J=6.0 and 1.0), 5.97 (dd, 0.63H, J=6.0 and 1.0), 5.89 (dd, 0.09H, J=10.0 and 3.0), 5.83 (dd, 0.07H, J=10.0 and 2.0), 5.39 (d, 0.09H, J=2.0), 5.35 (t, 0.07H, J=1.0), 4.25 (d, 0.09H, J=12.0), 4.06 (t, 0.06H, J=7.0), 3.98 (d, 0.07H, J=12.0), 3.85 (d, 0.07H, J=12.0), 3.82 (dd, 0.09H, J=12.0 and 1.5), 3.77 (d, 0.63H, J=12.0), 3.76 (d, 0.21H, J=12.0), 3.68 (d, 0.63H, J=12.0), 3.67 (d, 0.21H, J=12.0), 0.174 (s, 1.44H), 0.170 (s, 7.56H).

5. Step (5)

(2R)-2,5-dihydro-5-acetoxy-2-(2-(trimethylsilyl) ethynyl)furan-2-yl)methyl acetate (Compound 13

7.3 g of DMAP was added to 635 mL of a dry THF solution containing 126 g of the mixture of Compounds 9 and 10 and cooled to 25° C. or lower. To this, 146 g of acetic anhydride was added at 35° C. or lower and agitated at 30° C. for 30 minutes. After confirming the end of the reaction by thin-layer chromatography, 200 mL of water and 1.8 L of a 1 N aqueous sodium hydroxide solution were added, followed by extraction with ethyl acetate. The organic layer was washed with water and then concentrated to obtain 152 g of a crude product of Compound 13 as a clear brown oily product (crude yield: 86.0%).

Compound 13:
$^1$H-NMR
δH (500 MHz; CDCl$_3$) 6.91 (t, 0.79H, J=1.0), 6.85 (t, 0.21H, J=1.0), 6.15 (dd, 0.21H, J=5.5 and 1.0), 6.00 (dd, 0.21H, J=5.5 and 1.0), 6.14 (dd, 0.79H, J=5.5 and 1.0), 5.96 (dd, 0.79H, J=5.5 and 1.0), 4.39 (d, 0.21H, J=11.5), 4.35 (d, 0.79H, J=11.5), 4.25 (d, 0.79H, J=11.5), 4.19 (d, 0.21H, J=11.5), 2.10 (s, 0.63H), 2.09 (s, 2.37H), 2.05 (s, 0.63H), 2.07 (s, 2.37H), 0.17 (s, 1.89H), 0.16 (s, 7.11H).

6. Step (6)

(R)-2,5-dihydro-5-(3,4-dihydro-5-methyl-2,4-dioxopyrimidin-1(2H)-yl)-2-(2-(trimethylsilyl)ethynyl)furan-2-yl)methyl acetate (Compound 20

7.14 L of an EDC solution containing 121 g of thymine and 588 g of BSA was heated to 40° C. and agitated for an hour. To this, 7.14 L of a dry THF solution containing 142 g of the crude product of Compound 13 and 139 g of TMSOTf were added and agitated at 0° C. for 30 minutes. After confirming the end of the reaction by thin-layer chromatography, 4.8 L of a saturated sodium bicarbonate solution, 4.8 L of water and 2.4 L of EDC were added to separate the organic layer. The obtained organic layer was washed with water and concentrated to obtain 169 g of a crude product of Compound 20 as yellow crystal (crude yield: 97.2%).

Compound 20:
¹H-NMR
δH (500 MHz; CDCl₃) 8.09 (brs, 0.43H), 8.05 (brs, 0.57H), 7.20 (d, 0.57H, J=1.0), 7.24 (d, 0.43H, J=1.0), 7.10 (dd, 0.43H, J=2.0 and 1.5), 7.05 (t, 0.57H, J=1.5), 6.21 (dd, 0.43H, J=4.0 and 2.0), 6.19 (dd, 0.57H, J=4.0 and 2.0), 5.94 (t, 0.57H, J=1.5), 5.93 (t, 0.43H, J=1.5), 4.57 (d, 0.43H, J=12.0), 4.42 (d, 0.57H, J=12.0), 4.23 (d, 0.57H, J=12.0), 4.22 (d, 0.43H, J=12.0), 2.10 (s, 1.29H), 2.08 (s, 1.71H), 1.920 (s, 1.71H), 1.918 (s, 1.29H), 0.20 (s, 5.13H), 0.18 (s, 3.87H).

7. Steps (7) and (8)

1-((2R,5R)-5-ethynyl-2,5-dihydro-5-(hydroxymethyl)furan-2-yl)-5-methylpyrimidine-2,4(1H,3H)-dione (Compound 31; β-form)

1-((2S,5R)-5-ethynyl-2,5-dihydro-5-(hydroxymethyl)furan-2-yl)-5-methylpyrimidine-2,4(1H,3H)-dione (Compound 32; α-form)

15 mL of water was added to 3.0 g of the crude product of Compound 20, and heated to 25° C. 30 mL of a 1 N aqueous sodium hydroxide solution was added and further agitated at 30° C. or lower for 30 minutes. After confirming the end of the reaction by thin-layer chromatography, the resultant was cooled to 15° C. or lower, added with 20 mL of 24% aqueous ammonia and agitated. Solid matter was filtrated away and the resulting aqueous solution was purified using Daisogel SP120 40/60 ODS B 500×70 mm I.D. The obtained fraction was freeze-dried to obtain 655.1 mg of the intended Compound 31 as pale yellow crystal (yield 32.0%).

Compound 31:
¹H-NMR
δH (500 MHz; DMSO-d6) 11.36 (brs, 1H), 7.58 (d, 1H, J=1.0), 6.88 (t, 1H, J=2.0), 6.35 (dd, 1H, J=5.5 and 2.0), 6.05 (dd, 1H, J=5.5 and 1.0), 5.47 (t, 1H, J=6.0), 3.69 (dd, 1H, J=12.5 and 6.0), 3.67 (s, 1H), 3.59 (dd, 1H, J=12.5 and 6.0), 1.71 (s, 3H).
¹H-NMR
δH (500 MHz; CD3OD) 7.71 (d, 1H, J=1.5), 7.03 (t, 1H, J=1.5), 6.32 (dd, 1H, J=6.0 and 2.0), 6.00 (dd, 1H, J=6.0 and 1.5), 3.82 (d, 1H, J=12.5), 3.75 (d, 1H, J=12.5), 3.08 (s, 1H), 1.82 (d, 3H, J=1.5).
¹³C-NMR
δC (125 MHz; DMSO-d6) 164.54, 151.51, 137.49, 136.23, 127.82, 109.72, 89.61, 87.28, 82.14, 78.12, 66.44, 12.92.

The invention claimed is:
1. A method for producing a compound represented by the following Formula (III):

(wherein, $R^1$ represents a hydrogen atom, $R^2$ represents a hydrogen atom, and $R^3$ represents a hydrogen atom or a trisubstituted silyl group), the method comprising the steps of:
(a) oxidizing a furfuryl alcohol of Formula (I):

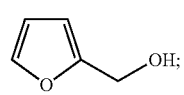

(b) acetylating the oxidized furfuryl alcohol to obtain the following compounds (±):

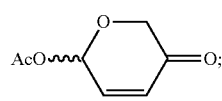

(c) treating the acetylated compounds with lipase to obtain the following acetylated compound (−):

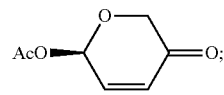

(d) introducing a triple bond-containing group into the acetylated compound (−), by causing the acetylated compound (−) to react with a compound represented by the following Formula:

(wherein, $R^3$ represents a hydrogen atom or a trisubstituted silyl group, and M represents a lithium atom, aluminum or monohalogenated magnesium); and
(e) treating the resulting product of step (d) with lipase, to obtain the compound represented by Formula (III).

2. A method for producing 4'-ethynyl-2',3'-didehydro-3'-deoxythymidine, comprising the steps of:
(a) introducing a triple bond-containing group into a (−)-enantiomer of an acetylated furfuryl alcohol compound represented by the following formula:

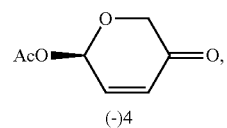 [SMILES: CC(=O)O[C@@H]1C=CC(=O)CO1]

by causing the (−)-enantiomer to react with a compound represented by the following Formula:

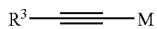

(wherein, $R^3$ represents a hydrogen atom or a trisubstituted silyl group, and M represents a lithium atom, aluminum or monohalogenated magnesium);

(b) treating the product of step (a) with lipase to obtain a compound represented by the following Formula (III):

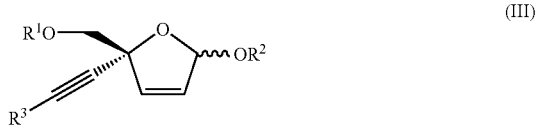

(wherein, $R^1$ represents a hydrogen atom, $R^2$ represents a hydrogen atom, and $R^3$ represents a hydrogen atom or a trisubstituted silyl group);

(c) causing the compound of Formula (III) to react with thymine; and (d) deprotecting the product of step (c) to obtain 4'-ethynyl-2',3'-didehydro-3'-deoxythymidine.

3. The method of claim 1, further comprising the step of acetylating the hydroxyl groups of the compound represented by Formula (III) after the step of treating with lipase.

4. The method of claim 2, further comprising the step of acetylating the hydroxyl groups of the compound represented by Formula (III) before the step of causing the compound of Formula (III) to react with thymine.

5. The method of claim 2, wherein the 4'-ethynyl-2',3'-didehydro-3'-deoxythymidine is purified by recrystallization.

6. The method of claim 3, wherein, after acetylating the compound represented by Formula (III), $R^3$ represents a trimethylsilyl group.

7. The method of claim 4, wherein, after acetylating the compound represented by Formula (III), $R^3$ represents a trimethylsilyl group.

* * * * *